United States Patent
Krebs et al.

(10) Patent No.: US 11,350,888 B2
(45) Date of Patent: Jun. 7, 2022

(54) RISK PREDICTION FOR SUDDEN CARDIAC DEATH FROM IMAGE DERIVED CARDIAC MOTION AND STRUCTURE FEATURES

(71) Applicants: Siemens Healthcare GmbH, Erlangen (DE); The Johns Hopkins University, Baltimore, MD (US)

(72) Inventors: Julian Krebs, Moers (DE); Hiroshi Ashikaga, Lutherville Timonium, MD (US); Tommaso Mansi, Plainsboro, NJ (US); Bin Lou, Princeton, NJ (US); Katherine Chih-ching Wu, Bel Air, MD (US); Henry Halperin, Baltimore, MD (US)

(73) Assignees: Siemens Healthcare GmbH, Erlangen (DE); The Johns Hopkins University, Baltimore, MD (US)

( * ) Notice: Subject to any disclaimer, the term of this patent is extended or adjusted under 35 U.S.C. 154(b) by 139 days.

(21) Appl. No.: 16/845,111

(22) Filed: Apr. 10, 2020

(65) Prior Publication Data

US 2021/0059612 A1  Mar. 4, 2021

Related U.S. Application Data

(60) Provisional application No. 62/895,048, filed on Sep. 3, 2019.

(51) Int. Cl.
*G06K 9/00* (2022.01)
*A61B 5/00* (2006.01)
(Continued)

(52) U.S. Cl.
CPC ............ *A61B 5/7275* (2013.01); *A61B 5/055* (2013.01); *A61B 5/4848* (2013.01); *A61B 5/7267* (2013.01); *G06T 7/0012* (2013.01); *G16H 30/40* (2018.01); *G16H 50/20* (2018.01); *G16H 50/30* (2018.01); *G06T 2207/10088* (2013.01); *G06T 2207/20081* (2013.01); *G06T 2207/20084* (2013.01); *G06T 2207/30048* (2013.01)

(58) Field of Classification Search
CPC .................................................. A61B 5/7275
See application file for complete search history.

(56) References Cited

U.S. PATENT DOCUMENTS

| | | | | |
|---|---|---|---|---|
| 2009/0162287 A1* | 6/2009 | Lerche | ................... | A61K 49/06 424/9.3 |
| 2015/0042646 A1* | 2/2015 | Comaniciu | .......... | A61B 6/5247 345/420 |

(Continued)

OTHER PUBLICATIONS

Myerburg, Robert J., Vivek Reddy, and Agustin Castellanos. "Indications for implantable cardioverter-defibrillators based on evidence and judgment." Journal of the American College of Cardiology 54.9 (2009): 747-763.

(Continued)

*Primary Examiner* — Oneal R Mistry (57) ABSTRACT

Systems and methods for personalized sudden cardiac death risk prediction that generates fingerprints of imaging features of cardiac structure and function. One or more fingerprints and clinical data may be used to generate a risk score. The output risk score may be used to predict the time of death in order to select high-risk patients for implantable cardioverter-defibrillator treatment.

16 Claims, 7 Drawing Sheets

(51) Int. Cl.
*A61B 5/055* (2006.01)
*G06T 7/00* (2017.01)
*G16H 30/40* (2018.01)
*G16H 50/30* (2018.01)
*G16H 50/20* (2018.01)

(56) References Cited

U.S. PATENT DOCUMENTS

| | | | | |
|---|---|---|---|---|
| 2015/0164453 | A1* | 6/2015 | Choi | A61B 5/0066 600/407 |
| 2018/0147305 | A1* | 5/2018 | Provost | A61K 51/0406 |
| 2020/0383584 | A1* | 12/2020 | Osman | A61B 5/055 |
| 2021/0137384 | A1* | 5/2021 | Robinson | A61B 5/0036 |

OTHER PUBLICATIONS

Epstein AE, DiMarco JP, Ellenbogen KA, Estes NM, Freedman RA, Gettes LS, Gillinov AM, Gregoratos G, Hammill SC, Hayes DL and others. 2012 ACCF/AHA/HRS focused update incorporated into the ACCF/AHA/HRS 2008 guidelines for device-based therapy of cardiac rhythm abnormalities. Circulation. 2013;127:e283-e352.

Sabbag, Avi, et al. "Contemporary rates of appropriate shock therapy in patients who receive implantable device therapy in a real-world setting: From the Israeli ICD Registry." Heart Rhythm 12.12 (2015): 2426-2433.

Punnoose, Lynn R., et al. "Heart failure with recovered ejection fraction: a distinct clinical entity." Journal of cardiac failure 17.7 (2011): 527-532.

Rijnierse, Mischa T., et al. "Usefulness of left atrial emptying fraction to predict ventricular arrhythmias in patients with implantable cardioverter defibrillators." The American journal of cardiology 120.2 (2017): 243-250.

Krebs, Julian, et al. "Probabilistic Motion Modeling from Medical Image Sequences: Application to Cardiac Cine—MRI." arXiv preprint arXiv:1907.13524 (Oct. 2019).

Lou, Bin, et al. "An image-based deep learning framework for individualising radiotherapy dose: a retrospective analysis of outcome prediction." The Lancet Digital Health 1.3 (2019): e136-e147.

* cited by examiner

RISK PREDICTION FOR SUDDEN CARDIAC DEATH FROM IMAGE DERIVED CARDIAC MOTION AND STRUCTURE FEATURES

CROSS REFERENCE TO RELATED APPLICATIONS

This application claims the benefit of U.S. Provisional Application No. 62/895,048 filed Sep. 3, 2019, which is hereby incorporated by reference in its entirety and relied upon.

GOVERNMENT INTERESTS

This invention was made with government support under HL103812 awarded by the National Institutes of Health. The government has certain rights in the invention.

BACKGROUND

The present embodiments relate to medical therapy or imaging.

Sudden cardiac death (SCD) is one of the largest causes of natural death. SCD occurs when the electrical system of the heart is malfunctioning, causing irregular heartbeats (arrythmias). Emergency treatment includes electric shocks (defibrillation) to restore the normal heart rhythm. For patients with a high risk for SCD, an implantable cardioverter-defibrillator (ICD) can be inserted as a preventive treatment. An ICD monitors the heart activity and can apply electric shocks in case of extreme arrythmias. Selecting patients for ICD treatment is a challenging task. It is crucial to predict the risk for SCD to justify potential complications that come along with an ICD treatment such as surgery risks, false shocks, and a shorter life expectancy. Accurate SCD risk prediction helps to select only patients for ICD who benefit from it.

One metric that has been used to prognosticate risk for SCD is left ventricular (LV) ejection fraction (EF). LVEF is a feature of cardiac structure and function. However, among patients receiving a primary prevention ICD based on LVEF, the rate of appropriate therapies is low. Many patients that receive ICD treatment do not require it. In addition, LVEF improvement occurs in up to 25-50% of patients and correlates with diminished SCD risk. Thus, LVEF is far from being a comprehensive feature to predict SCD.

Imaging features of cardiac structure and function, such as the extent of heterogeneous myocardial tissue (gray zone) on late gadolinium enhancement (LGE) cardiac magnetic resonance (CMR), right ventricular (RV) and left atrial (LA) function, have been found to be independent predictors of SCD. Nevertheless, it is unknown how best to simultaneously assess the multiple interacting imaging and clinical features associated with increased SCD risk.

SUMMARY

Systems, methods, and computer readable media are provided for personalized SCD risk prediction using machine learning-based methods. Networks are trained to generate fingerprints of cardiac structure and/or cardiac function from medical imaging data. A separate network is used to generate a risk score from one or more of the fingerprints and clinical data. The output risk score may be used to predict, for example, a time of death in order to select high-risk patients for ICD treatment.

In a first aspect, a method is provided for risk prediction for sudden cardiac events, the method comprising: acquiring, using a medical imaging device, image data of a patient comprising at least a sequence of image frames of a heart of the patient; a function fingerprint from the image data using a function fingerprint network configured to generate cardiac function fingerprints when input a sequence of image data; calculating, by the processor, a sudden cardiac risk value from the function fingerprint fingerprint using a risk assessment network configured to estimate sudden cardiac events from input cardiac function fingerprints; and determining, by the processor, whether or not to proceed with therapy like implantable cardioverter-defibrillator treatment based on the sudden cardiac risk value.

In an embodiment, the method further includes determining, by a processor, a structure fingerprint from the image data using a structure fingerprint network configured to generate cardiac structure fingerprints when input image data. In an embodiment, the method may further include acquiring clinical data about the patient; wherein the risk assessment network is configured to estimate sudden cardiac events based further on clinical data.

In an embodiment, the function fingerprint network is configured as an encoder-decoder network that is trained as a temporal variational autoencoder that encodes cardiac motion detected in the sequence of images in a low-dimensional matrix. In an embodiment, the structure fingerprint network is configured as an encoder-decoder network that is trained to encode cardiac structure from masked images. In an embodiment, the risk assessment network comprises an encoder-decoder network trained by a nonlinear Cox regression model for future clinical events. In an embodiment, the risk assessment network is configured to output an estimated first hospitalization due to acute decompensated heart failure. In an embodiment, the sudden cardiac risk value predicts a timing of a future sudden cardiac event.

The structure fingerprint network and function fingerprint network may be trained prior to training the risk assessment network or the structure fingerprint network, function fingerprint network, and risk assessment network are trained together in an end-to-end fashion.

In a second aspect, a method is provided for configuring a risk prediction network to estimate a risk of sudden cardiac death, the method comprising: acquiring, by a processor, labeled image data for a patient cohort with known future events; training, by the processor, a cardiac motion network to generate a function fingerprint from the labeled image data; training, by the processor, a cardiac structure network to generate a structure fingerprint from the labeled image data; training, by the processor, the risk estimation network to generate sudden cardiac death risk values based on the function fingerprints and the structure fingerprints for each patient in the patient cohort; and determining, by the processor, a risk threshold for classification based on the sudden cardiac risk values generated by the risk estimation network for the patient cohort. Training a respective network comprises inputting data, comparing an output to the input data, a label for the input data, or the input data and the label, and adjusting the respective network based on the comparison.

In an embodiment, the labeled image data comprises MRI CINE and LGE image data. In an embodiment, the method further includes acquiring clinical data for the patient cohort including age, sex, and underlying health issues for each patient of the patient cohort. The risk regression network is trained to generate sudden cardiac death risk values based further on the clinical data.

In an embodiment, the cardiac function network is configured as an encoder-decoder network that is trained as a temporal variational autoencoder that encodes cardiac motion detected in a sequence of images from the labeled image data in a low-dimensional matrix.

In an embodiment, the cardiac structure network is configured as an encoder-decoder network that is trained to encode cardiac structure from masked images of the labeled image data.

In an embodiment, the risk estimation network comprises an encoder-decoder network trained by a nonlinear Cox regression model for future clinical events.

In a third aspect, a system is provided for cardiac risk prediction, the system includes a medical imaging scanner configured to acquire image data of a patient; a first trained network, stored in a memory, and configured to generate a structure fingerprint when input the image data; a second trained network, stored in the memory, configured to generate a function fingerprint when input the image data; a third trained network, stored in the memory, configured to calculate a sudden cardiac risk value when input the structure fingerprint and the function fingerprint; and a processor configured to generate a risk assessment for whether or not to proceed with implantable cardioverter-defibrillator treatment for the patient based on the sudden cardiac risk value.

In an embodiment, the system further includes a display configured to display the risk assessment.

In an embodiment, the third trained network is further configured to input clinical data about the patient.

In an embodiment, the image data comprises MRI CINE and LGE image data.

In an embodiment, the sudden cardiac risk value comprises an estimated first hospitalization due to acute decompensated heart failure.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION

Embodiments provide different networks trained as task-specific fingerprint extractors, for example, a motion fingerprint extractor and a structure fingerprint extractor. The motion fingerprint extractor is trained to extract a fingerprint related to the cardiac function from a sequence of images. The structure fingerprint extractor is trained to determine a structure fingerprint from one or more images. The function fingerprint and the structure fingerprint are input with additional clinical data about the patient into a risk estimation network that is configured to identify the risk to the patient. The output of the risk estimation network may be used for assistance in selecting a therapy.

Embodiments may be implemented in cardiology systems to provide a risk estimation of SCD to support physicians in decision-making for or against ICD treatment. Embodiments provide a sensitive and specific test for SCD risks to improve patient ICD implant triage, thus improving QoL, reducing medical errors, reducing costs, and reducing the number of unnecessary ICD implants. The risk of SCD prediction performance is improved by using the task-specific cardiac function and structure fingerprints instead of only using manually extracted features. The combination of function and structure fingerprints provides an accurate estimation that can be quickly and efficiently obtained. Embodiments use high-dimensional multi-modal data and are able to use more features for risk prediction than a standard model. In addition, cumbersome data processing to extract hand-crafted features such as LA strain is not required. The configuration of the networks and/or the learning mechanisms used to train the networks and implement the system and method provide various benefits.

Figure 1:
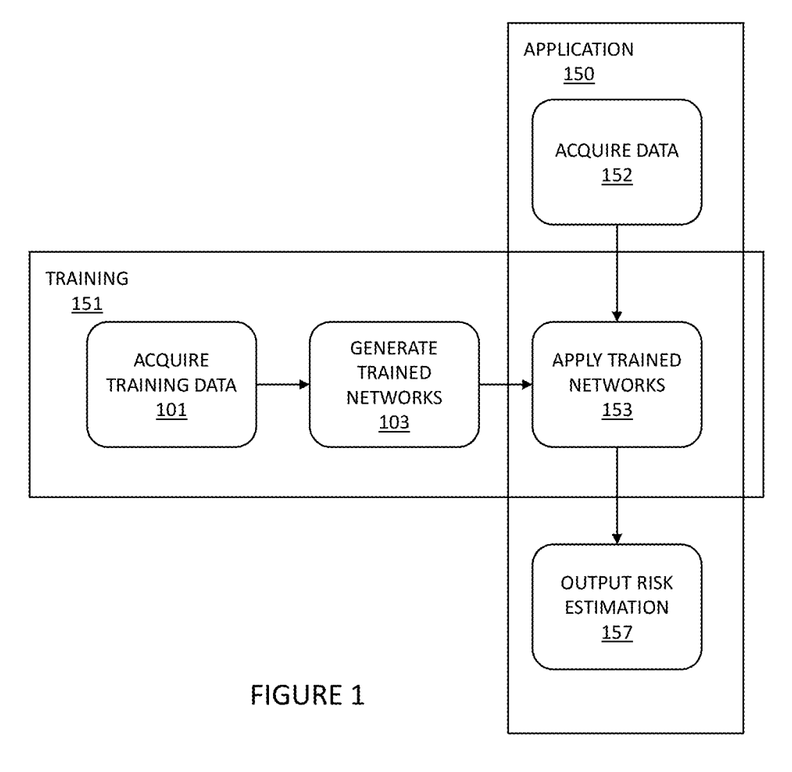
FIG. 1 depicts an example flowchart for risk prediction for sudden cardiac death from image derived cardiac motion and structure features according to an embodiment.

FIG. 1 depicts an example flowchart for risk prediction for sudden cardiac death from image-derived cardiac motion and structure features. The flowchart includes two stages, a training stage 151 and an application stage 150. The training stage 151 includes generating or training the networks using a collection of training data (labeled data). Each of the networks (motion fingerprint, structure fingerprint, risk estimation) may be trained separately or the entire system may be trained end-to-end. The flowchart also includes the application stage 150 for applying the generated/trained networks to new unseen (unlabeled) data. The training stage 151 includes acquiring 101 training data and inputting the training data into each network in order to generate 103 trained networks. The output of the training stage 151 is a collection of trained networks that are applied 153 in the application stage 150. The application stage 150 includes acquiring 152 image data of an unseen patient, applying 153 the trained networks that were trained during the training stage 151 to the image data, and outputting 157 a risk assessment for the patient. The risk assessment may be used to generate a plan for therapy or intervention.

The training stage 151 may be performed at any point prior to the application stage 150. The training stage 151 may be repeated after new training data is acquired. The application stage 150 may be performed at any point after the training stage 151 generates the trained networks and image data of a patient is acquired. The application stage 150 may be performed, for example, during (e.g. real time) or directly after a medical procedure is performed or as part of planning for a patient. Alternatively, the application stage 150 may be performed at a later point using data acquired from an imaging scan and stored, for example, in a PACS.

Figure 2:
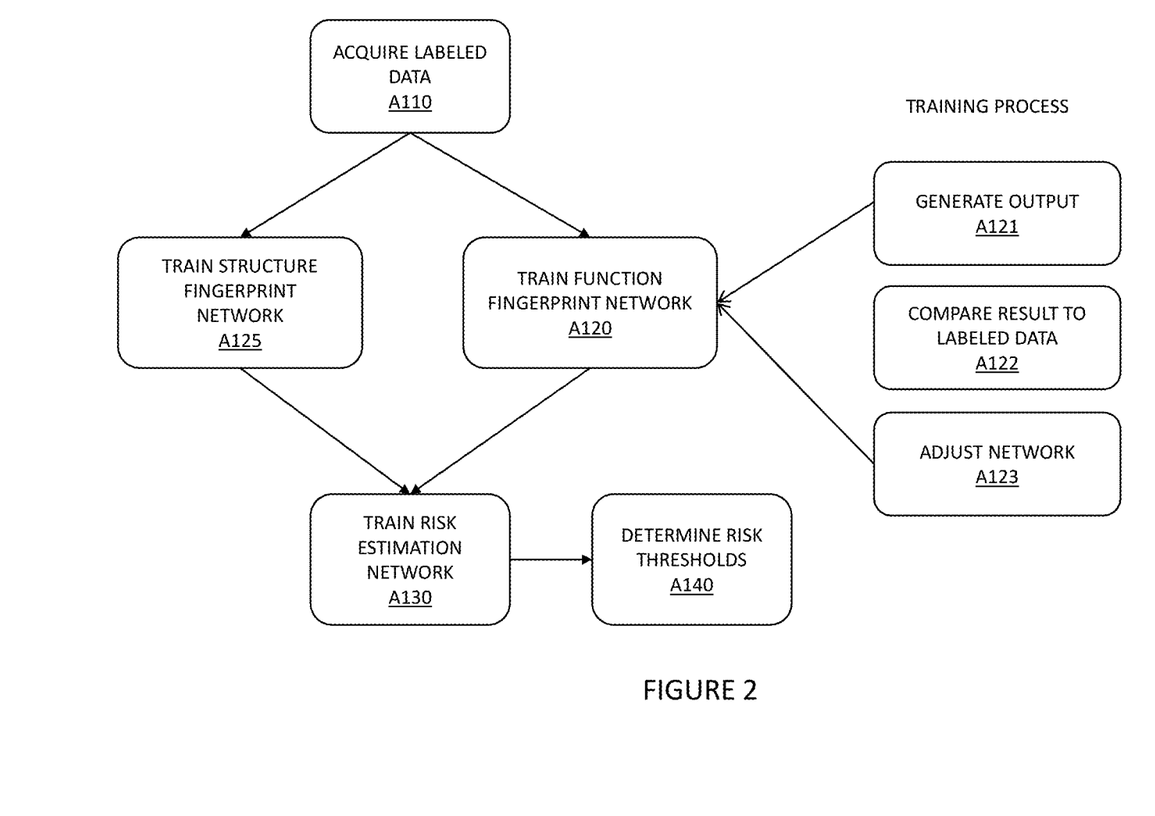
FIG. 2 depicts a workflow for training a network to determine an SCD risk value for a patient according to an embodiment.

FIG. 2 depicts a workflow for training a network to determine an SCD risk value for a patient. The acts are performed by the system of FIGS. 3, 4, 6, 7, other systems, a workstation, a computer, and/or a server. Additional, different, or fewer acts may be provided. The acts are performed in the order shown (e.g., top to bottom) or other orders. Certain acts may be omitted or changed depending on the results of the previous acts. Referring back to FIG. 1, each of the networks are trained during the training stage prior to the application stage. The workflow described below includes acquiring training data, training the fingerprint networks, and then training the risk estimation network. The fingerprint networks may be trained in any order. In an embodiment, each of the fingerprint networks may be trained prior to training of the risk estimation network. Alternatively, the entire system or network may be trained end-to-end. In an embodiment, one or both of the fingerprint networks may be trained and used. For example, the risk estimation network may use an output from the function fingerprint network, the structure fingerprint network, or both.

At act A110, a plurality of annotated/labeled image data is acquired. To train the network, ground truth labels are used. The ground truth labels may be manually generated or automatically generated using different techniques. Ground truth data/gold standard data is data that includes correct or reasonably accurate labels. As an example, for image data that is used in the structure fingerprint network, the training data includes the original data and associated segmented data. The segmented data may be generated and labeled using any method or process, for example, manually by an operator or automatically by one or more automatic methods. For the function fingerprint, the training data may include, for example information relating to the strain and strain rate of LV, LA, and RV. For the risk estimation network, the training data may include labels relating to known events, e.g. SCD events, for a patient cohort. The training data may be acquired at any point prior to inputting the training data into the trained network. The training data may be updated after acquiring new data. The updated training data may be used to retrain or update the trained networks.

In an embodiment, publicly available data collections may be used. Ground truth labels may be added as needed. The datasets differ in several aspects. Each data collection may include different types of data including different information. In some data collections, due to follow-up scans, there are multiple images per patient. Patient-wise splits may be used to separate the patients into training, validation, and test sets. In an embodiment, the system gathers MRI data, including cine-CMR and LGE images, and clinical data for a patient cohort with known future events.

In an embodiment, the image data is magnetic resonance imaging (MRI) data acquiring using a MR scanner. MRI allows accurate quantification of both cardiac anatomy and function (e.g. cine imaging) and pathological tissues such as scars (late gadolinium enhancement (LGE) imaging). In an embodiment, the image data includes both cine images and LGE images. Cine images are short sequences that show heart motion throughout the cardiac cycle. Cine images are obtained with ECG triggered segmented imaging by dividing the cardiac cycle into multiple segments (frames) to produce a series of images that can be displayed as a movie (cine). The cardiac cycle begins with the R wave of the ECG, ends with the subsequent R wave, and may be divided into 10 to 35 segments, depending on the heart rate. Each image in the cine may be composed of information gathered over several heart beats allowing for a movie to be acquired with a breath hold of 10 to 20 seconds depending on the sequence. The output data is a sequence of individual frames. The sequence of individual frames is used to determine a fingerprint for the cardiac function, valvular function, and/or movement of blood through the heart. The function fingerprint, as will be described below, may be used for risk assessment.

Late gadolinium enhancement imaging (LGE) provides one or more images. LGE imaging uses the delayed wash in and wash out in tissue with an increased proportion of extracellular space. In the setting of an acute myocardial infarction, this is caused by cellular necrosis and lysis, and edema, while in the chronic infarcted tissue, the fibrous scar tissue with its increased extracellular space is the basis. The increased amount of gadolinium is demonstrated by T1-weighted imaging, in the time period of 10-30 min after contrast administration. LGE may be used for scar detection based on differences in the volume of distribution of gadolinium, an extracellular agent. The LGE images may be used to determine a fingerprint for the cardiac structure that is used for risk assessment.

At acts A120 and A125, the fingerprint networks are trained using the acquired labeled image data. The networks may be trained separately, in parallel, or end to end with the risk estimation network. The training process requires a dataset that contains paired images and labels for training and testing, an optimizer (e.g. stochastic gradient descent, Adam), and a loss function to update the model parameters. The function accounts for the error of the network prediction in each iteration during training, providing signals for the optimizer to update the network parameters through backpropagation. The goal of training is to find proper values of the learnable network parameters to minimize the loss function. The training process may be iterative including repeating inputting image data, generating (A121) an output, comparing (A122) the output along with any labels, and adjusting (A123) the network for each piece of training data. The training process proceeds until a set number of iterations has been performed or the network reaches a convergence.

Each of the networks may be defined as a plurality of sequential feature units or layers. Sequential is used to indicate the general flow of output feature values from one layer to input to a next layer. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on the input data. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Various units or layers may be used, such as convolutional, pooling (e.g., max pooling), deconvolutional, fully connected, or other types of layers. Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape indication. For transposed convolution to reconstruct, the level of abstraction reverses. Each unit or layer reduces the level of abstraction or compression.

One or more of the networks may be configured as variations of autoencoder networks. Autoencoders are neural networks that are configured to find efficient representations of a dataset. Autoencoders include an encoder network that maps images to low-dimensional latent vectors, and a decoder network which approximates the original image from the latent vector. Autoencoders transforms data linearly, and then apply a non-linear rectification, for example, a sigmoid function. As an example, one objective function for an autoencoders is the expected mean square error between an input image and reconstructed images using the trained features. Autoencoders may be trained using stochastic gradient descent or other methods to learn the features leading to the best reconstruction.

In an embodiment, one or more of the networks may be configured as a variational autoencoder. A variational autoencoder (VAE) is a generative model that predicts parameters of the variational distribution. A VAE models the generation of y as conditioned on an unobserved, latent variable z by p, and seeks to maximize the data log likelihood p. The main principle of VAE as opposed to a regular autoencoder is to introduce an approximate posterior q with variational parameters predicted by a neural network to address the intractability of the true posterior p in maximum likelihood inference. A VAE may be understood as a regularized version of an autoencoder, where q can be considered the encoder and p the decoder. A conditional variational autoencoder (CVAE) may also be used that models latent variables and data, both conditioned to some random variables.

Training of AE, VAE, CVAE or other types of autoencoders may be prone to over-fitting for high-dimensional input data. Sparsity or denoising techniques (e.g., sparse denoising AE (SDAE)) may be used to constrain the freedom of parameters and force learning of interesting structures within the data. Enforcing sparsity within hidden layers (i.e., only a small number of units in hidden layers are activated at one time) may also regularize the network. In other embodiments, at least one unit is a convolution with ReLU activation or is a batch normalization with a ReLU activation followed by a convolution layer (BN+LeakyRU+ convolution). Max pooling, up-sampling, down-sampling, and/or SoftMax layers or units may be used. Different units may be of the same or different type.

Referring back to FIG. 2, at act A125, the function fingerprint network is trained as an autoencoder that encodes the motion in a low-dimensional matrix, e.g. the "function fingerprint". The function fingerprint may be configured to emulate a probabilistic motion model. The function fingerprint network may be configured to take as input a 4-chamber view cine CMR and output dense deformation fields depicting the cardiac motion. LV, LA, and RV strain and strain rates may be derived from the estimated deformations. The accuracy of the function fingerprint may be validated by comparing the strain, strain rate, and segmentation of LV, LA, and RV in both the input labeled cine series and the output cine series.

Figure 3A:
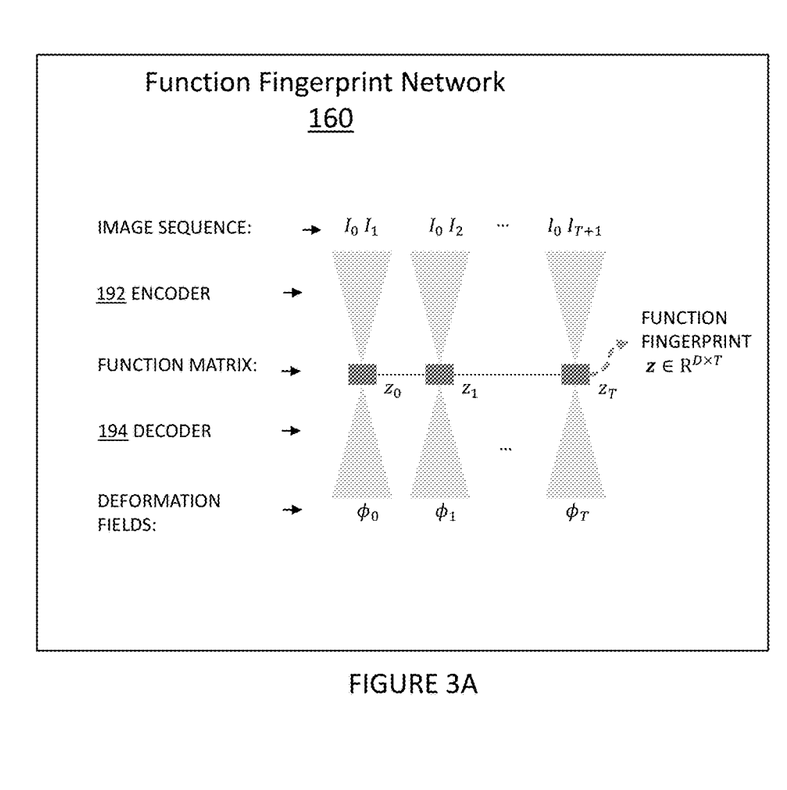
FIG. 3A depicts an example function fingerprint network according to an embodiment.

FIG. 3A depicts an example function fingerprint network 160 configured to generate a function fingerprint. The inputs to the function fingerprint network 160 may be a sequence of acquired image pairs (I0, It) with t∈[1, T] from image sequences of length T. The outputs of the function fingerprint network 160 are a sequence of dense deformation fields $\phi t$ (between (I0, It)) and a compact deformation representation $zt \in RD$ of dimensionality D per timestep t. The sequence of encoded representations zt are combined in the motion matrix $z \in RD \times T^-$ with $T^-=T-1$ and D latent dimensions depicting the cardiac motion. The function fingerprint network 160 may be trained using a conditional variational autoencoder including an encoder and decoder.

The encoder 192 with network weights maps each of the image pairs independently to a latent space. The encoder 192 approximates the posterior distribution of the latent variable model. The latent vectors are jointly mapped to the motion matrix or motion fingerprint by conditioning the vectors on all past and future time steps and on the normalized time. The regularizing network with weights are realized using a temporal convolutional network. The decoder 194 inputs the features maps of the last block of the encoder network 192 and outputs a predicted image. The decoder 194 with trainable network weights aims to reconstruct the fixed image by warping the moving image with the deformation. The deformation is extracted from the temporally regularized codes. The decoder 194 is further conditioned on the moving image by concatenating the features at each scale with down-sampled versions. The decoder 194 then approximates the data likelihood.

Referring back to FIG. 2, at act A125, the structure fingerprint network is trained as an autoencoder that encodes the structure in one or more features, e.g. the "structure fingerprint". The structure fingerprint may be coded as a standard and denoising autoencoder or a probabilistic network (e.g. a variational autoencoders VAE). The structure fingerprint network may be trained to generate segmentation masks that are compared to the ground truth annotated image data. Training objectives include L1 or L2 reconstruction loss terms of a segmented image output by the network compared to the input image. The loss may be, for example, calculated as:

$$\mathcal{L}_{struc} = \frac{1}{N}\sum_{i=1}^{N} \|mLGE_i - mLGE_i^*\|^2 \text{ for } N \text{ } LGE \text{ Training image.}$$

The accuracy of the structure fingerprint may be validated by comparing the extent of the gray zone of each slice in both the input and the output images.

The segmentation loss may use any segmentation-based evaluation metric, or even multiple metrics predicted simultaneously. Different metrics that may be used may include DICE, Jaccard, true positive rate, true negative rate, modified Hausdorff, volumetric similarity, or others. DICE is a measure of the comparison between two different images or sets of values. The Jaccard index (JAC) between two sets is defined as the intersection between them divided by their union. True Positive Rate (TPR), also called Sensitivity and Recall, measures the portion of positive voxels in the ground truth that are also identified as positive by the segmentation being evaluated. Analogously, True Negative Rate (TNR), also called Specificity, measures the portion of negative voxels (background) in the ground truth segmentation that are also identified as negative by the segmentation being evaluated.

Figure 3B:
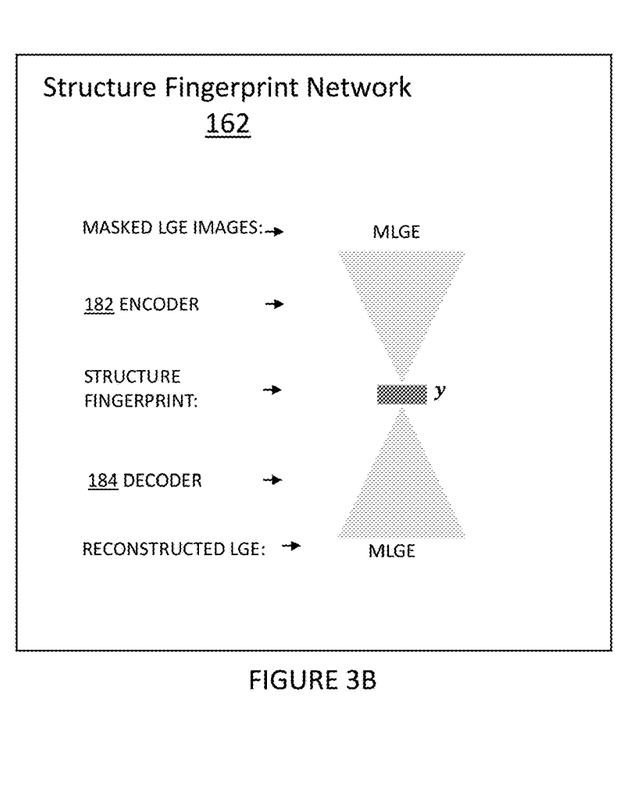
FIG. 3B depicts an example structure fingerprint network according to an embodiment.

FIG. 3B depicts an example structure fingerprint network 162. The structure fingerprint network 162 is defined as a plurality of sequential feature units or layers. The encoder 182 of the structure fingerprint network 162 may use a DenseNet architecture. A DenseNet connects each layer in a network to every other layer in a feed-forward fashion. For each layer in the DenseNet, the feature-maps of all preceding layers are used as inputs, and the output feature-map of that layer is used as input into all subsequent layers. In the DenseNet, for each layer, the feature maps of all preceding layers are used as inputs, and its own feature maps are used as inputs into all subsequent layers. To reduce the size of the network, the DenseNet may include transition layers. The layers include convolution followed by average pooling. The transition layers reduce height and width dimensions but leave the feature dimension the same. The encoder 182 is configured to encode the structure features of the input image as one or more feature maps. The output of the encoder 182 may be used as the structure fingerprint y.

The output of the encoder network 182 is used as an input to the decoder network 184. The output of the decoder network 184 is a segmented image/reconstructed LGE image that may or not be shown to a user. During application 150, only the encoder 182 may be used. The decoder network 184 may not be used during application 150, but rather only used during training 151. The decoder network 184 inputs the features maps of the last block of the encoder network 182 and outputs predicted segmented masks for the input image data, for example, the LGE MRI data.

At act A130, the risk estimation network is configured. The non-linear risk regression model is configured based on observed events using extracted fingerprints and clinical features if available. The risk estimation network may be configured as an autoencoder network that reduces the fingerprints' dimensionalities in order to identify the risk. The risk predictor is trained using multi-task learning by aiming to reconstruct the fingerprints and to predict the risk r at the same time.

In an embodiment, a nonlinear Cox regression model for future clinical events is used to train the risk estimation network. The primary endpoint is SCD, and the secondary endpoints include the first hospitalization due to acute decompensated heart failure, inappropriate ICD shock, and all-cause mortality. Cox regression (or proportional hazards regression) is a method for investigating the effect of several variables upon the time a specified event takes to happen. In the context of an outcome such as death, e.g. SCD, this is also known as Cox regression for survival analysis. For the Cox regression model, T denotes a continuous non-negative random variable describing the failure time of an event (i.e., time-to-event) in a system. The probability density function of t; that is, the actual survival time is f(t). The survival function, S(t), is probability that the failure occurs later than time t. The related hazard function, h(t), denotes the probability density of an event occurring around time t, given that it has not occurred prior to time t. In survival analysis, each instance is characterized by a 3-tuple (ti, i, xi) where xi contains the covariates and ti is either the time of the event (such as metastasis or death) when i=1 or the censoring time when i=0. For each patient i, the objective is to model its associated hazard hi(t). This time depending function gives the probability of a patient i to have the event at time t knowing that he has not yet experienced the event before.

The encoding and decoding branches of the risk autoencoder are denoted by $q_\theta$ and $p_\omega$. A third network may also be applied to obtain the risk score $q_\theta(x)$ from the latent space of the autoencoder. The risk predictor is trained using multi-task learning by aiming to reconstruct the fingerprints and to predict the risk r at the same time. Thus, the loss function LRisk contains 2 terms, one for the fingerprint reconstruction Lrec and one for risk prediction Lrisk. For training the risk estimation network, the loss function may be represented by:

$$\mathcal{L} = \mathcal{L}_{rec} + \gamma \mathcal{L}_{risk}$$

where the reconstruction term:

$$\mathcal{L}_{rec} = \frac{1}{N}\sum_{i=1}^{N} \|x_i - p_\omega(q_\theta(x_i))\|^2$$

and with risk regression term, the negative log partial likelihood as survival function over N censored training samples:

$$\mathcal{L}_{risk} = \Sigma_{i=1}^{N} \delta_i [q_\theta(x_i) - \log \Sigma_{j=1}^{N} R_{ij} \exp(q_\theta(x_j))]$$

Using censoring indicator $\delta_i=1$ if censored, risk matrix $R_{ij}=1$ if $t_j \geq t_j$ and $R_{ij}=0$ if $t_j < t_j$, based on N samples per batch. This represents a non-linear Cox proportional hazard model.

Figure 4:
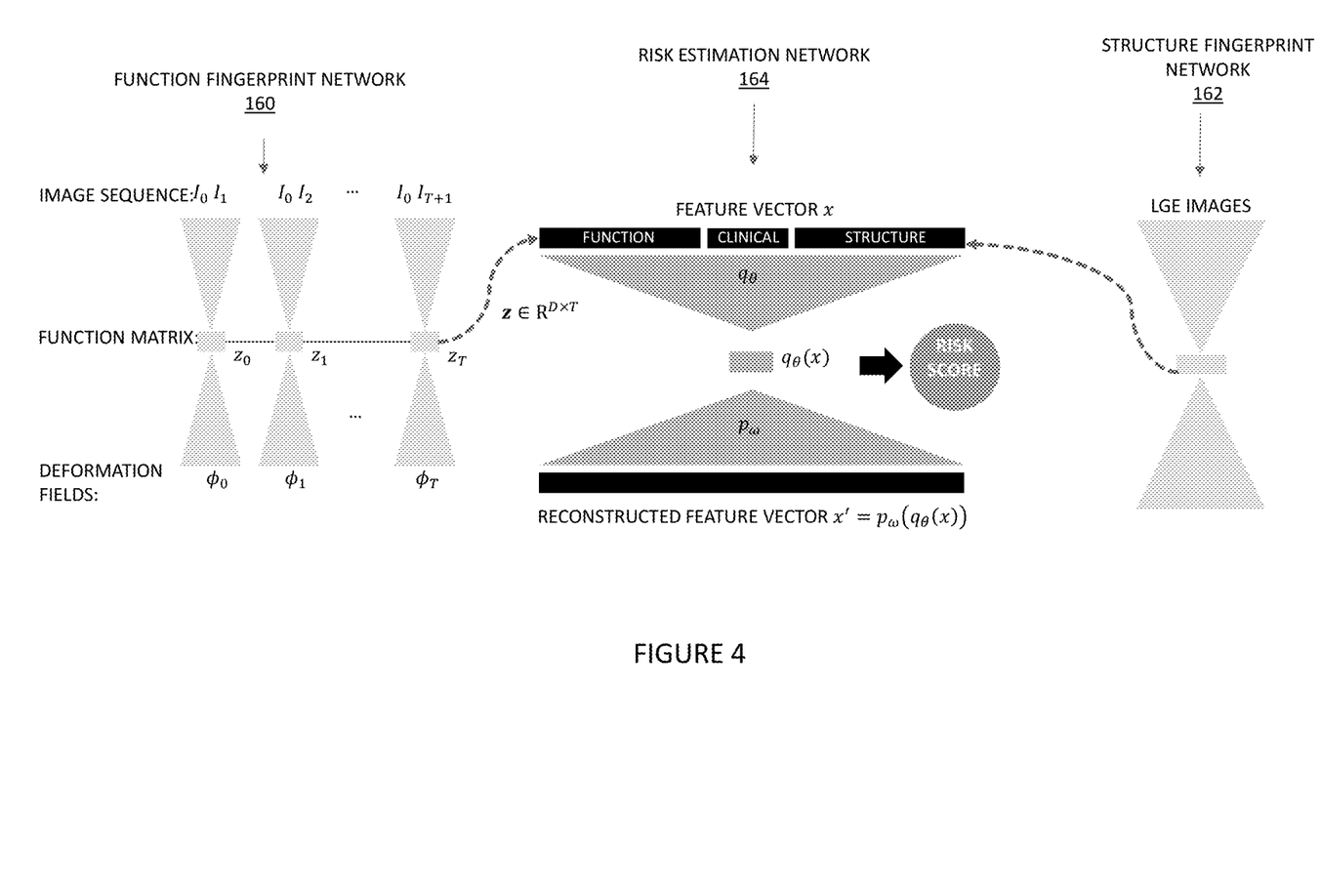
FIG. 4 depicts an example of the training process for the risk estimation network according to an embodiment.

Each of the fingerprint networks and risk estimation network may be either trained independently or in an end-to-end fashion where all loss terms are combined in a single weighted loss function. FIG. 4 depicts an example of the training process for the risk estimation network 164. The function network and the structure network are trained and input data into the risk estimation network 164 which outputs a risk score that can be classified according to obtained risks scores from the training data.

Alternative deep architectures may be used for one or more of the networks such as CNN, deep belief nets (DBN), or other deep networks. CNN learns feed-forward mapping functions while DBN learns a generative model of data. In addition, CNN uses shared weights for all local regions while DBN is a fully connected network (e.g., including different weights for all regions of an image). The training of CNN is entirely discriminative through backpropagation. DBN, on the other hand, employs the layer-wise unsupervised training (e.g., pre-training) followed by the discriminative refinement with backpropagation if necessary. In an embodiment, the arrangement of the trained network is a fully convolutional network (FCN). Alternative network arrangements may be used, for example, a 3D Very Deep Convolutional Networks (3D-VGGNet). VGGNet stacks many layer blocks containing narrow convolutional layers followed by max pooling layers. A 3D Deep Residual Networks (3D-ResNet) architecture may be used. A Resnet uses residual blocks and skip connections to learn residual mapping.

At act A140, risk thresholds may be determined for classification based on SCD risk scores experienced in the training data. The risk estimation may include an estimation that a SCD event may occur during a certain time frame, for example, 1 year, 2 years, 5 years, or other period of time.

The risk estimation and classification may be based on the known events that have occurred for the patient cohort.

Figure 5:
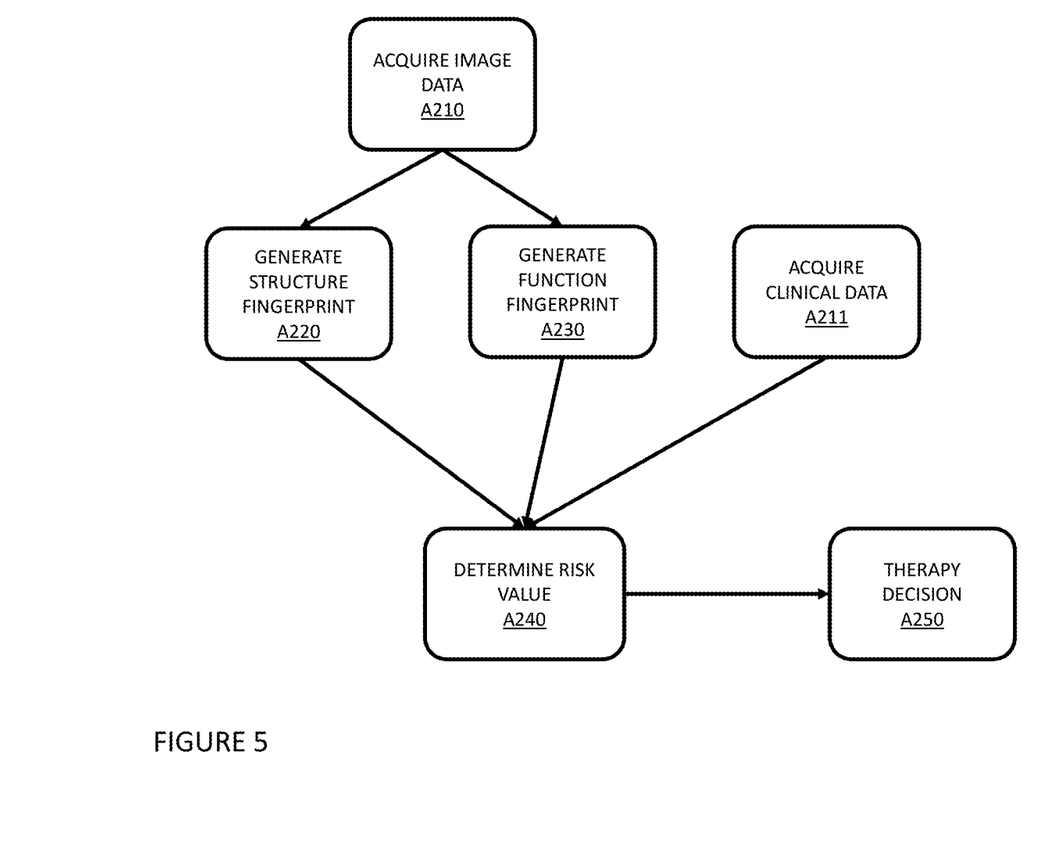
FIG. 5 depicts a flow chart diagram of one embodiment of a method for application of risk prediction for sudden cardiac death.

FIG. 5 is a flow chart diagram of one embodiment of a method for application of risk prediction for sudden cardiac death. The method of FIG. 5 is performed by a medical system 100, such as the medical system 100 of FIG. 7. FIG. 7 depicts one embodiment of a medical system 100 for risk prediction for sudden cardiac death. The medical system 100 of FIG. 6 includes the display 102, memory 106, processor 104, and medical imaging device 110. A patient 120 is depicted as being prepared to be or being scanned by the medical imaging device 110. The medical imaging device 100 may be a scanner for one of a medical imaging modalities (e.g., CT scanner, magnetic resonance (MR) scanner, positron emission tomography (PET) scanner, single photon emission computed tomography (SPECT) scanner, ultrasound scanner, x-ray scanner, or other diagnostic imaging scanner 110) and/or a medical therapy system (e.g., x-ray therapy system). Other devices may be used to perform any of the acts.

The method of FIG. 5 is performed in the order shown (e.g., top to bottom or numerical), but other orders may be used. The method of FIG. 5 describes the application stage 150 of FIG. 1. The networks as described may already have been pretrained during a training stage 151, for example as described in FIG. 2. Additional, different, or fewer acts may be provided. As an example, act A220 or A230 may not be performed. In act A240, the risk assessment network may input a structure fingerprint, a function fingerprint, or both. Additional fingerprints may also be generated and used as input.

In the examples described below, MRI cardiac image data is used as the image data. The networks are therefore also trained and optimized using a dataset of annotated MRI cardiac images. Other types of image data may be used such as cardiac ultrasound images. In the described embodiments, certain machine learning techniques are also used to optimize the internal parameters of the networks. Different machine learning techniques may be used with different types of images. The networks may be trained in an end-to-end training fashion or separately. As an example, both fingerprint extractor networks may be trained in a task-specific way, such that features are optimally suited for input into the risk estimation network 164.

At act A210, image data of a patient is acquired by a medical imaging device. The image data 201 is data representing a two-dimensional image or a three-dimensional volume of the object or patient. The data may be in any format. While the terms image and imaging are used, the image or imaging data may be in a format prior to actual display of the image. For example, the imaging data may be a plurality of scalar values representing different locations in a Cartesian or polar coordinate format different than a display format. As another example, the imaging data may include a plurality of shades of grey values output to a display for generating the image in the display format. The imaging data is a dataset that may be used for imaging, such as scan data or a generated image representing the patient. In an embodiment, the image data is magnetic resonance imaging (MRI) data acquiring using a MR scanner. The MRI data may include both cine imaging and LGE images. In an embodiment, clinical data about the patient may also be acquired (A211). The clinical data may include data such as sex, age, health factors, image-derived features (such as gray volume, ejection fraction), and other patient data.

At act A220, the processor determines a structure fingerprint from the acquired image data. The structure fingerprint is determined using a structure fingerprint network 162 trained to input imaging data and output a structure fingerprint. The structure fingerprint network 162 may be configured as an autoencoder network that includes an encoder network that maps images to low-dimensional latent vectors and a decoder network that approximates the original image from the latent vector. The low-dimensional latent vectors may be used as the "structure fingerprint." The inputs of the structure fingerprint network 162 are masked LGE images (containing only myocardium) acquired at act A210.

At act A230, the processor determines a function fingerprint from the acquired image data. The function fingerprint is output by a function fingerprint network 160 configured as an encoder-decoder network that represents a latent variable model. In an embodiment, the function fingerprint network 160 takes as input 4-chamber view cine CMR and outputs dense deformation fields depicting the cardiac motion. In an embodiment, the function fingerprint network 160 may have been trained as a temporal variational autoencoder which encodes the motion in a low-dimensional matrix which represents the function fingerprint.

At act A240, the processor generates a risk value for the patient as a function of the structure fingerprint, function fingerprint, and clinical data for the patient. A risk estimation network 164 is configured to receive the structure fingerprint, the function fingerprint, and clinical data and to output a survival risk score that is equivalent to a logarithm of a hazard ratio in a Cox regression analysis. The scalar risk score is used to classify the outcome risk for the patient at test time. The risk estimation network 164 may be configured as an autoencoder neural network that reduces the fingerprints' dimensionality to determine the survival risk score. The risk estimation network 164 may provide an estimation of when a SCD event will occur for the patient.

The risk estimation network 164 may be configured as a non-linear risk regression model that is trained by a nonlinear Cox regression model for future clinical events. The primary output of the model is SCD estimation. secondary outputs may include the first hospitalization due to acute decompensated heart failure, inappropriate ICD shock, other heart failure related deaths, and all-cause mortality. The risk estimation network 164 may be either trained independently or in an end-to-end fashion where weighted summands of all fingerprint network loss terms are added. In the latter case, fingerprints are fine-tuned for task-specific needs of personalized SCD risk prediction.

At act A250, an ICD treatment is suggested based on the SCD risk. For patients with a high risk for SCD, an ICD may be inserted as a preventive treatment. An ICD monitors the heart activity and can apply electric shocks in case of extreme arrythmias. However, ICD treatment includes such downsides as surgery risks, false shocks, and a shorter life expectancy. The SCD risk value generated at act A140 may be used as part of the determination of whether or not to proceed with ICD treatment or to proceed with an alternative therapy. Accurate SCD risk prediction helps to select only patients for ICD who benefit from it.

Figure 6:
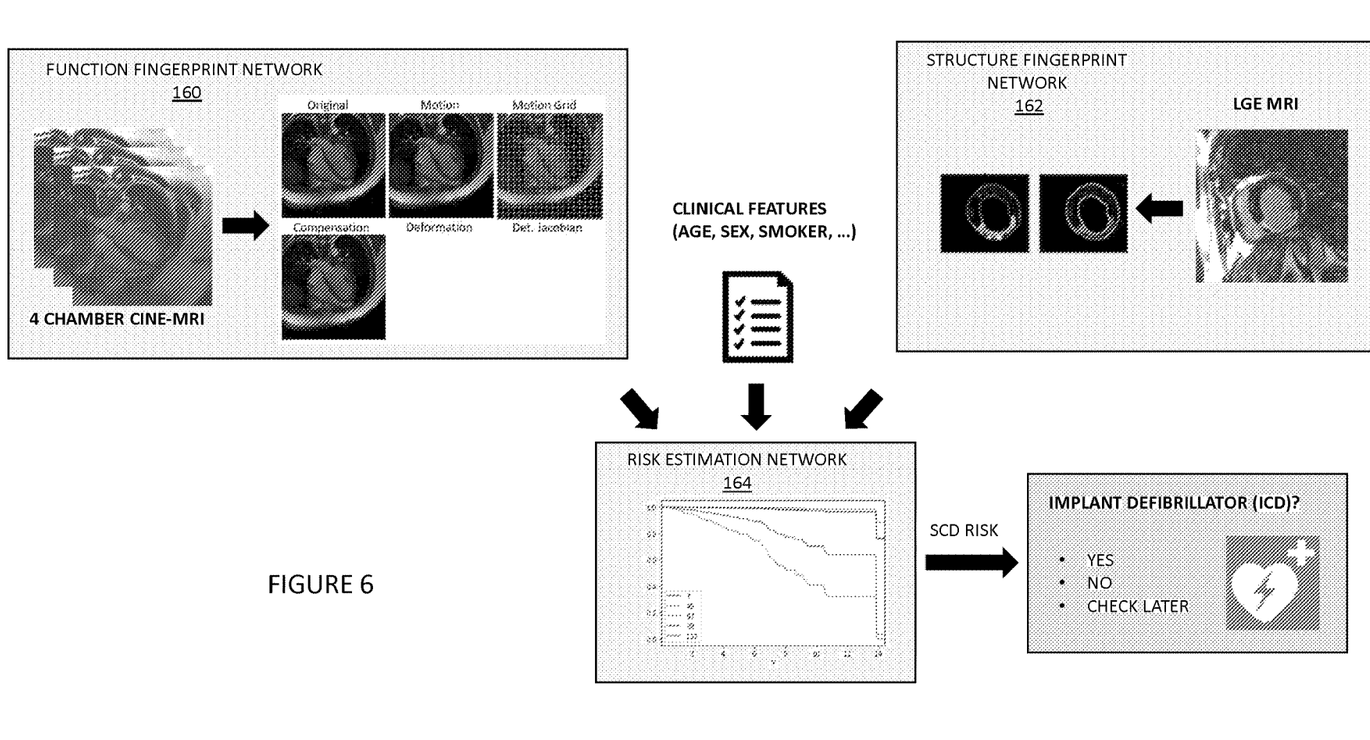
FIG. 6 depicts one embodiment of a workflow for SCD risk estimation.
Figure 7:
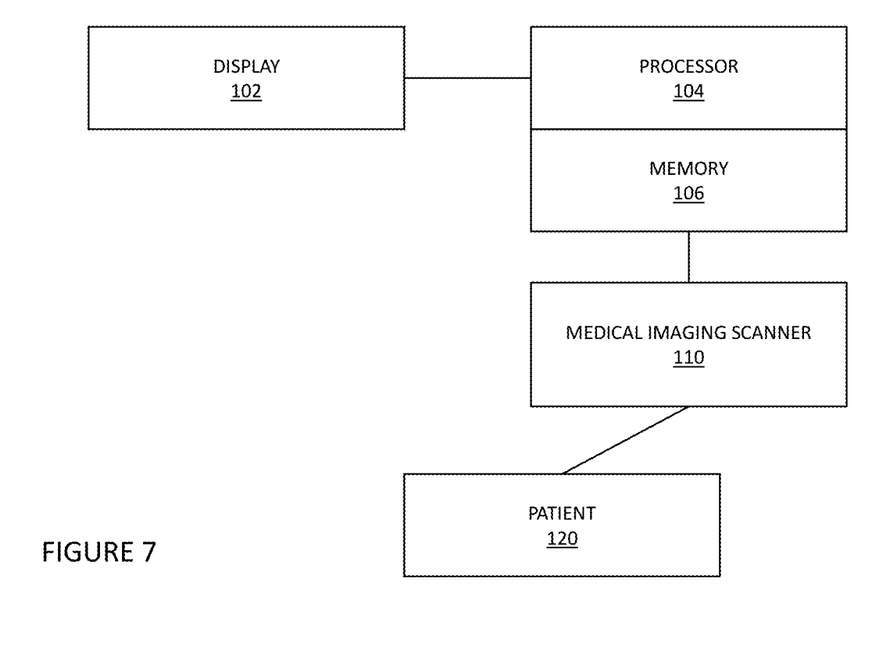
FIG. 7 depicts a medical system for SCD risk prediction according to an embodiment.

FIG. 6 depicts one embodiment of a workflow for SCD risk estimation. In FIG. 6, 4 chamber cine-MRI data and LGE MRI data is acquired and input into the function fingerprint network 160 and structure fingerprint network 162 respectively. The two fingerprints and clinical data are input to the risk estimation network 164, which outputs a SCD risk. The output SCD risk is used to determine whether or not to implant a defibrillator.

FIG. 7 depicts a medical system 100 for SCD risk prediction according to an embodiment. The medical system 100 includes the display 102, memory 106, processor 104, medical scanner 110, and a patient 120. The display 102, processor 104, and memory 106 may be part of the medical system 100, a computer, server, workstation, or other system for diagnosis or treatment. A workstation or computer without the medical system 100 may be used with the medical system 100. Additional, different, or fewer components may be provided. For example, a computer network is included for remote processing or storage. As another example, a user input device (e.g., keyboard, buttons, sliders, dials, trackball, mouse, or other device) is provided for user alteration or setting for configuring the medical system 100.

The processor 104 is a control processor, image processor, general processor, digital signal processor, three-dimensional data processor, graphics processing unit, application specific integrated circuit, field programmable gate array, artificial intelligence processor, digital circuit, analog circuit, combinations thereof, or other now known or later developed device for processing surface data. The processor 104 is a single device, a plurality of devices, or a network. For more than one device, parallel or sequential division of processing may be used. In one embodiment, the processor 104 is a control processor or other processor of a medical therapy system 100. The processor 104 operates pursuant to and is configured by stored instructions, hardware, and/or firmware to perform various acts described herein.

The processor 104 is configured to train and apply two encoder-decoder neural networks that are configured to extract cardiac structure and function fingerprints. The processor 104 is configured to train and apply a third network that predicts the SCD risk given the two fingerprints and optionally other clinical features as input.

The processor 104 may be configured to train/configure/adjust the networks using machine learning techniques. The training procedure includes: gathering cine-CMR, LGE images and optionally clinical data for a patient cohort with known future events (censored data), pretraining unsupervised motion and structure models to obtain function and structure fingerprints, train non-linear risk regression model based on observed events using extracted fingerprints and clinical features if available, and determine risk threshold(s) for classification based on SCD risk scores experienced in the training data. During inference, the SCD risk of new patients is classified according to the network prediction risk score given cine-CMR, LGE images and clinical data.

The processor 104 is configured to learn a structure fingerprint from acquired LGE CME, a function fingerprint from cine CMR, and combine both for personalized SCD risk prediction using a risk estimation network 164. The risk estimation network 164 takes the motion fingerprint and the structure fingerprint as inputs and predicts the survival risk score r which is equivalent to the logarithm of the hazard ratio in the Cox regression analysis. This scalar risk score r allows to classify the outcome risk for a new patient at test time. The risk model is realized as autoencoder neural networks that reduce the fingerprint's dimensionality in order to retrieve the risk r.

The display 102 is a CRT, LCD, projector, plasma, printer, tablet, smart phone or other now known or later developed display device for displaying the output. The display 102 is configured by loading an image into a buffer. The display 102 is configured to display an image of the patient or signaling.

The acquired image data, labeled image data, networks, network structures, and/or other information are stored in a non-transitory computer readable memory, such as the memory 106. For example, the configuration, nodes, weights, and other parameters of the structure fingerprint network 162, the function fingerprint network 160, and the risk estimation network 164 may be stored in the memory 106. The memory 106 is an external storage device, RAM, ROM, database, and/or a local memory (e.g., solid state drive or hard drive). The same or different non-transitory computer readable media may be used for the instructions and other data. The memory 106 may be implemented using a database management system (DBMS) and residing on a memory, such as a hard disk, RAM, or removable media. Alternatively, the memory 106 is internal to the processor 104 (e.g. cache).

The instructions for implementing the processes, methods, and/or techniques discussed herein are provided on non-transitory computer-readable storage media or memories, such as a cache, buffer, RAM, removable media, hard drive, or other computer readable storage media (e.g., the memory 106). The instructions are executable by the processor 104 or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor or processing strategy and may be performed by software, hardware, integrated circuits, firmware, micro code, and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The medical system 100 includes a diagnostic imaging scanner 110, such as CT, MR, PET, or SPECT system or a therapeutic radiation scanner, such as an x-ray or particle therapy system. The diagnostic imaging scanner 110 may be configured to acquire MR images, for example, LGE image data and CINE image data. The diagnostic imaging scanner 110 may alternatively be configured to acquire other types of image data such as 2D/3D ultrasound, as well as 4D CT that includes image data from which at least some cardiac motion can be reliably estimated. The diagnostic imaging scanner 110 operates pursuant to one or more settings and scanning parameters to treat or image a patient. The settings and scanning parameters control the location in the patient being scanned, the type of scan (e.g., pulse sequence), and/or radiation dose. The diagnostic imaging scanner 110 is configured by setting values of variables to operate in a particular way appropriate for the particular patient. Once configured by the settings, the medical system 100 treats or images the patient. The diagnostic imaging scanner 110 is configured to generate diagnostic image information. The patient 120 is imaged by the diagnostic imaging scanner 110 using the settings.

Various improvements described herein may be used together or separately. Although illustrative embodiments of the present invention have been described herein with reference to the accompanying drawings, it is to be understood that the invention is not limited to those precise embodi-

What is claimed is:

1. A method for risk prediction for sudden cardiac events, the method comprising:
acquiring, using a medical image scanner, image data of a patient comprising at least a sequence of image frames of a heart of the patient;
determining, by a processor, a function fingerprint from the image data using a first network configured to generate cardiac function fingerprints in response to input of the sequence of image frames;
determining, by the processor, a structure fingerprint from the image data using a second network configured to generate cardiac structure fingerprints in response to input of the image data;
calculating, by the processor, a sudden cardiac risk value from the function fingerprint and the structure fingerprint using a third network configured to estimate sudden cardiac events from cardiac structure fingerprints and function fingerprints; and
determining, by the processor, whether or not to proceed with implantable cardioverter-defibrillator treatment based on the sudden cardiac risk value.

2. The method of claim 1, further comprising:
acquiring clinical data about the patient; wherein the third network is configured to estimate sudden cardiac events based further on clinical data.

3. The method of claim 1, wherein the second network is configured as an encoder-decoder network that is trained to encode cardiac structure from masked images.

4. The method of claim 1, wherein the image data comprises MRI cine data for input into the first network and LGE image data for input into the second network.

5. The method of claim 1, wherein the first network and the second network are trained prior to training the third network.

6. The method of claim 1, wherein the first network, the second network, and the third network are trained together end to end.

7. The method of claim 1, wherein the first network is configured as an encoder-decoder network that is trained as a temporal variational autoencoder that encodes cardiac motion detected in the sequence of image frames in a low-dimensional matrix.

8. The method of claim 1, wherein the third network comprises an encoder-decoder network trained by a nonlinear Cox regression model for future clinical events.

9. A method for configuring a risk estimation network to estimate a risk of sudden cardiac death, the method comprising:
acquiring, by a processor, labeled image data for a patient cohort with known future events;
training, by the processor, a cardiac function network to generate a function fingerprint from the labeled image data;
training, by the processor, a cardiac structure network to generate a structure fingerprint from the labeled image data, wherein the cardiac structure network is configured as an encoder-decoder network that is trained to encode cardiac structure from masked images of the labeled image data; and
training, by the processor, the risk estimation network to generate sudden cardiac death risk values based on the function fingerprint and the structure fingerprint for each patient in the patient cohort.

10. The method of claim 9, further comprising:
acquiring clinical data for the patient cohort including age, sex, and underlying health issues for each patient of the patient cohort;
wherein the risk estimation network is trained to generate sudden cardiac death risk values based further on the clinical data.

11. The method of claim 9, wherein the cardiac function network is configured as an encoder-decoder network that is trained as a temporal variational autoencoder that encodes cardiac motion detected in a sequence of images from the labeled image data in a low-dimensional matrix.

12. The method of claim 9, wherein the risk estimation network comprises an encoder-decoder network trained by a nonlinear Cox regression model for future clinical events.

13. The method of claim 9, further comprising:
determining, by the processor, a risk threshold for classification based on sudden cardiac risk values generated by the risk estimation network for the patient cohort.

14. A system for cardiac risk prediction, the system comprising:
a medical imaging scanner configured to acquire image data of a patient;
a first machine-trained network stored in a memory and configured to generate a function fingerprint when input the image data;
a second machine-trained network stored in the memory and configured to generate a structure fingerprint when input the image data;
a third machine-trained network stored in the memory and configured to calculate a sudden cardiac risk value when input the function fingerprint and the structure fingerprint; and
a processor configured to generate a risk assessment for whether or not to proceed with implantable cardioverter-defibrillator treatment for the patient based on the sudden cardiac risk value.

15. The system of claim 14, wherein the third machine-trained network is further configured to input clinical data about the patient.

16. The system of claim 14, wherein the image data comprises MRI CINE and LGE image data.

* * * * *